(12) United States Patent
Singh

(10) Patent No.: US 9,192,510 B2
(45) Date of Patent: Nov. 24, 2015

(54) LOCALIZED HYPOTHERMIA TO TREAT WEIGHT DISORDERS

(75) Inventor: Vijay P. Singh, Pittsburgh, PA (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1043 days.

(21) Appl. No.: 13/212,819

(22) Filed: Aug. 18, 2011

(65) Prior Publication Data

US 2012/0046718 A1     Feb. 23, 2012

Related U.S. Application Data

(60) Provisional application No. 61/374,797, filed on Aug. 18, 2010.

(51) Int. Cl.
*A61F 7/12* (2006.01)
*A61F 7/00* (2006.01)

(52) U.S. Cl.
CPC .......... *A61F 7/123* (2013.01); *A61F 2007/0056* (2013.01); *A61F 2007/126* (2013.01)

(58) Field of Classification Search
CPC .............. A61F 7/123; A61F 2007/126; A61F 2007/0056; A61F 2007/029
See application file for complete search history.

(56) References Cited

U.S. PATENT DOCUMENTS

| | | | |
|---|---|---|---|
| 3,254,652 A | 6/1966 | Smith et al. | |
| 3,460,538 A | 8/1969 | Armstrong | |
| 3,768,484 A | 10/1973 | Gawura | |
| 4,133,315 A * | 1/1979 | Berman et al. | 606/193 |
| 4,543,089 A | 9/1985 | Moss | |
| 4,718,429 A * | 1/1988 | Smidt | 607/104 |
| 5,007,437 A | 4/1991 | Sterzer | |
| 5,151,100 A | 9/1992 | Abele et al. | |
| 6,427,089 B1 | 7/2002 | Knowlton | |
| 6,558,412 B2 | 5/2003 | Dobak, III | |
| 6,589,271 B1 | 7/2003 | Tzeng et al. | |
| 6,726,708 B2 | 4/2004 | Lasheras | |
| 6,818,011 B2 | 11/2004 | Dobak, III | |
| 7,063,718 B2 | 6/2006 | Dobak, III | |
| 7,077,825 B1 | 7/2006 | Stull | |
| 7,758,623 B2 | 7/2010 | Dzeng et al. | |
| 7,896,009 B2 * | 3/2011 | Stull | 128/898 |
| 8,231,664 B2 | 7/2012 | Kulstad et al. | |
| 8,361,132 B2 | 1/2013 | Arad | |
| 2003/0220674 A1 * | 11/2003 | Anderson et al. | 607/96 |
| 2004/0210214 A1 * | 10/2004 | Knowlton | 606/41 |
| 2004/0215180 A1 * | 10/2004 | Starkebaum et al. | 606/32 |
| 2005/0096638 A1 * | 5/2005 | Starkebaum et al. | 606/2 |
| 2005/0203501 A1 * | 9/2005 | Aldrich et al. | 606/27 |
| 2005/0240250 A1 | 10/2005 | Dobak, III | |
| 2007/0198071 A1 * | 8/2007 | Ting et al. | 607/96 |

(Continued)

FOREIGN PATENT DOCUMENTS

SU     1378835 A1     3/1988

OTHER PUBLICATIONS

Buchan, "Gastric freezing in the rat," *Gut*, 1965;6(5):494-499.

(Continued)

*Primary Examiner* — Kaitlyn Smith
(74) *Attorney, Agent, or Firm* — Mueting, Raasch & Gebhardt, P.A.

(57) ABSTRACT

Materials and Methods for producing localized hypothermia in a patient for treatment of a weight disorder (e.g., obesity).

19 Claims, 6 Drawing Sheets

(56) References Cited

U.S. PATENT DOCUMENTS

| | | | |
|---|---|---|---|
| 2007/0225781 A1* | 9/2007 | Saadat et al. | 607/105 |
| 2007/0265608 A1* | 11/2007 | Hernandez | 606/21 |
| 2008/0077211 A1* | 3/2008 | Levinson et al. | 607/108 |
| 2008/0287839 A1* | 11/2008 | Rosen et al. | 601/18 |
| 2009/0018623 A1* | 1/2009 | Levinson et al. | 607/96 |
| 2009/0018626 A1* | 1/2009 | Levinson et al. | 607/96 |
| 2009/0048514 A1* | 2/2009 | Azhari et al. | 600/439 |
| 2009/0105696 A1* | 4/2009 | Lee et al. | 606/3 |
| 2009/0118722 A1* | 5/2009 | Ebbers et al. | 606/21 |
| 2009/0149929 A1* | 6/2009 | Levinson et al. | 607/99 |
| 2009/0312597 A1* | 12/2009 | Bar et al. | 600/37 |
| 2009/0312676 A1* | 12/2009 | Rousso et al. | 601/15 |
| 2010/0030190 A1* | 2/2010 | Singh | 604/516 |
| 2010/0152824 A1* | 6/2010 | Allison | 607/113 |
| 2010/0280582 A1* | 11/2010 | Baker et al. | 607/113 |
| 2011/0238051 A1* | 9/2011 | Levinson et al. | 606/22 |
| 2011/0239682 A1* | 10/2011 | Raines et al. | 62/259.3 |
| 2012/0221083 A1* | 8/2012 | Cruzada | 607/112 |
| 2012/0239123 A1* | 9/2012 | Weber et al. | 607/104 |
| 2012/0290051 A1* | 11/2012 | Boyden et al. | 607/113 |
| 2013/0013037 A1* | 1/2013 | Adams | 607/114 |
| 2013/0131764 A1* | 5/2013 | Grove | 607/108 |
| 2013/0204331 A1* | 8/2013 | Harikrishna et al. | 607/107 |
| 2013/0289438 A1* | 10/2013 | Lyon | 600/549 |
| 2014/0051905 A1* | 2/2014 | Sako et al. | 600/12 |
| 2014/0277308 A1* | 9/2014 | Cronise et al. | 607/112 |

OTHER PUBLICATIONS

Cho et al., "Endoscopic cryotherapy for the management of gastric antral vascular ectasia," *Gastrointest. Endosc.*, 2008;68(5):895-902.

Gaggiotti et al., "Adjustable Totally Implantable Intragastric Prosthesis (ATIIP)—:Endogast® for Treatment of Morbid Obesity: One year follow-up of a Multicenter Prospective Clinical Survey," *Obes. Surg.*, 2007;17(7):949-956.

Genco et al., "BioEnterics® Intragstric Balloon (BIB®): a short-term, double-blind, randomised, controlled, crossover study on weight reduction in morbidly-obese patients," *Int. J. Obes. (Lond.)*, 2006;30:129-133.

Lunding et al., "Pressure-induced gastric accommodation studied with a new distension paradigm. Abnormally low accommodation rate in patients with functional dyspepsia," *Scand. J. Gastroenterol.*, 2006;41:544-552.

Matsuoka et al., "Effects of Moderate Hypothermia on Proinflammatory Cytokine Production in a Rat Model of Caerulein-Induced Pancreatitis," *Pancreas*, 2003;26(1):e12-e17.

McFarland et al., "The clinical place of gastric hypothermia," *Ann. R. Coll. Surg. Engl.*, 1968; delivered at the Royal College of Surgeons of England on Apr. 27, 1967;42(3):182-205.

Melnyk et al., "Gastric Freezing in Dogs," *Ann. Surg.*, 1965;162:135-144.

Mundt et al., "Fundal dysaccommodation in functional dyspepsia: head-to-head comparison between the barostat and three-dimensional ultrasonographic technique," *Gut*, 2006;55:1725-1730.

Nabseth et al., "Studies on the effect of intragastric cooling on acute experimental pancreatitis," *Surgery*, 1960;47(4):542-547.

Patiutko et al., "Ways of improving results of gastro-pancreatoduodenal resection in tumors of the bilio-pancreatoduodenal area," *Khirurgila (Mosk)*, 1995:(3):26-29 (*abstract only*).

Preuss et al., "Pancreatic changes in cases of death due to hypothermia," *Forensic Science International*, 2007;166:194-198.

Rakonczay et al., "The Effects of Hypo- and Hypothermic Pretreatment on Sodium Taurocholate-Induced Acute Pancreatitis in Rats," *Pancreas*, 2002;24(1):83-89.

Roddenberry et al., "Hypothermia in the Treatment of Acute Pancreatitis," *J. Am. Med. Assoc.*, 1967;201(11):825-827.

Sipos et al., "Temperature-dependent activation of trypsin by calcium," *Biochem. Biophys. Res. Commun.*, 1968;31(4):522-527.

Stiff et al., "Hypothermia and acute pancreatitis: myth or reality?" *J.Royal Soc. Med.*, 2003;96(5):228-229.

Symbas et al., "Influence of Hypothermia on Pancreatic Function," *Ann. Surg.*, 1961;154(4):509-515.

Wels et al., "Hypothermia in acute hemorrhagic pancreatitis," *Arch. Surg.*, 1962;85:817-821.

White et al., "Problems and Complications of Gastric Freezing," *Annals of Surgery*, 1964;159(5):765-768.

\* cited by examiner

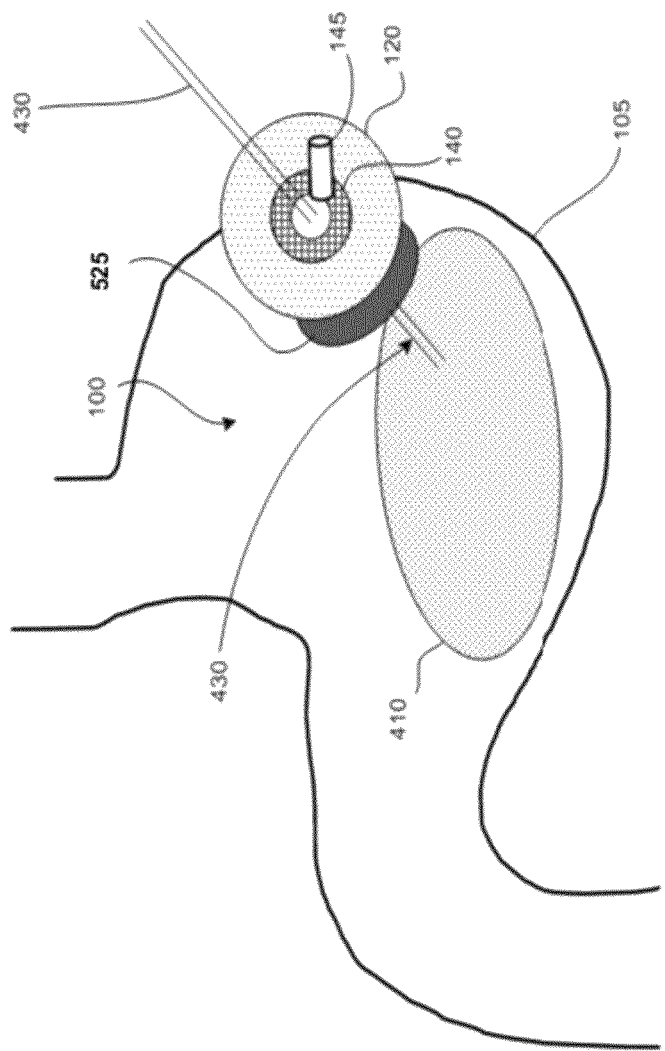

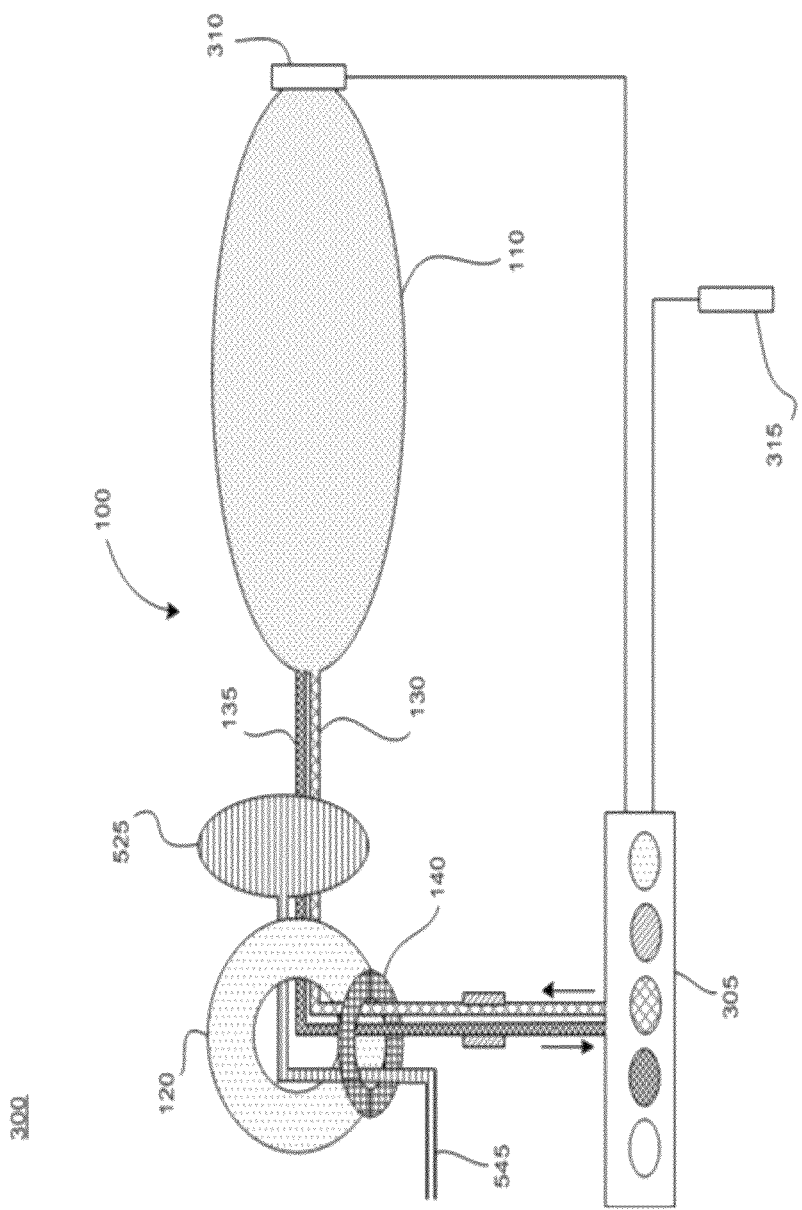

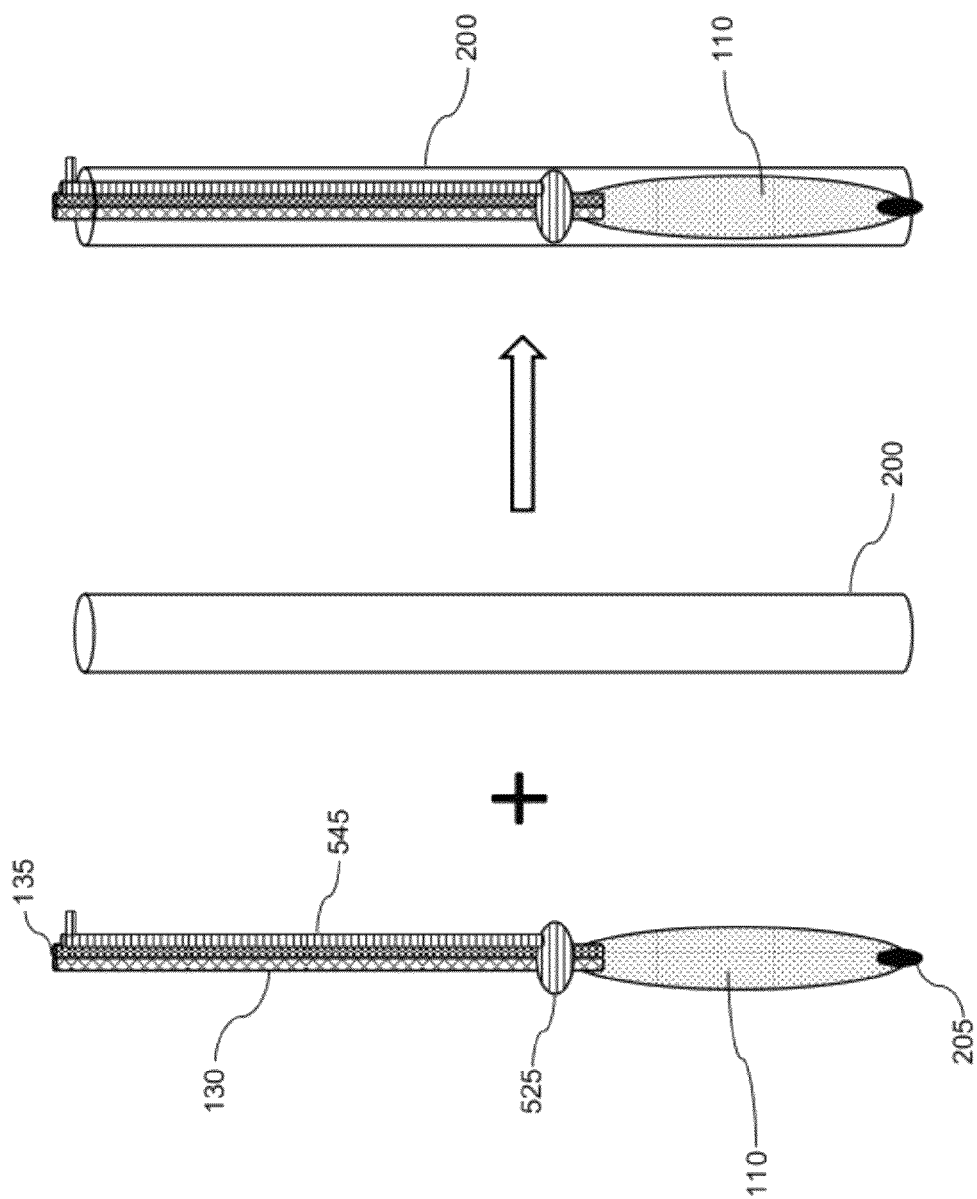

LOCALIZED HYPOTHERMIA TO TREAT WEIGHT DISORDERS

CROSS-REFERENCE TO RELATED APPLICATIONS

This application claims priority from U.S. Provisional Application Ser. No. 61/374,797, filed Aug. 18, 2010.

TECHNICAL FIELD

This document relates to materials and methods for using localized hypothermia, while avoiding generalized hypothermia, to treat weight disorders such as obesity.

BACKGROUND

An average human adult requires about 2000-2500 Kcal/day. If the average human burns about the same amount per day, a net balance is generally maintained and the person's weight should remain steady. However, many people consume more calories than they burn. This can lead to obesity, a medical condition in which excess body fat has accumulated to the extent that it may have an adverse effect on health, leading to a reduced life expectancy and/or increased health problems, such as heart disease, type 2 diabetes, sleep issues, and cancer. A person can be considered obese if the person's body mass index (BMI; a measure of body fat based on height and weight) is greater than 30 kg/m$^2$.

The current epidemic of obesity and its numerous complications have resulted in enormous economic and healthcare burdens. Treatments for obesity often include dieting and/or increasing physical exercise, but such conventional therapies can be ineffective and/or difficult to comply with. Anti-obesity drugs also can be taken to reduce appetite or inhibit fat absorption, and in severe cases, surgery can be performed. Weight loss supplements and surgery have their own complications, however.

SUMMARY

This document is based in part on the development of a method for using localized hypothermia to prevent or reverse excessive weight gain. The rapid rate of calorie loss through localized hypothermia can provide an attractive way to lose weight. Although potential complications may arise, such complications can be minimized by maintaining localized hypothermia in a very controlled manner with several safety features.

The devices and procedures disclosed herein can be used to stimulate weight loss through conductive heat loss, and can be more effective than dietary measures and exercise alone. Moreover, the devices and procedures do not require patients to take weight loss supplements or undergo invasive surgery.

In a general aspect, the methods described herein can include inserting into a patient (e.g., a patient having a BMI of 30 kg/m$^2$ or more) an apparatus comprising one or more expandable, compliant balloons; irrigating at least one of the balloons with a fluid having an inflow temperature that is below the patient's body temperature; and removing the fluid from the balloon at an outflow temperature that is greater than the inflow temperature. The methods also may include monitoring the amount of calories lost in a particular time frame; and determining whether the amount of calories lost is within a predetermined range that permits weight loss but prevents hypothermia.

In another general aspect, the methods can include inserting into a patient an apparatus comprising at least one heat transfer device such that the heat transfer device is in heat transfer communication with at least an organ or a portion of an organ in the patient; and adjusting the temperature of the heat transfer device so that at least part of the heat transfer device has a temperature that is below the patient's body temperature. The methods also can include monitoring the amount of calories lost in a specified time frame; and determining whether the calories lost is within a predetermined range that permits weight loss but prevents hypothermia.

Thus, this document features methods for treating a weight disorder in a patient in need thereof, comprising subjecting an organ or tissue of the patient to localized hypothermia. The weight disorder can be obesity, and the patient can have a body mass index of at least 30 kg/m$^2$.

The methods can include: (a) inserting into the patient a device having an inflatable member having an interior and an exterior, and an inflow conduit and an outflow conduit in fluid communication with the interior of the inflatable member; (b) infusing the inflatable member with a fluid passed through the inflow conduit, wherein the fluid is at a temperature from about 4° C. to about 35° C.; and (c) removing fluid from the inflatable member through the outflow conduit. The fluid can have a temperature of about 30-35° C. when it is infused into the balloon. The fluid can be water. The inflow conduit can have a first flexible tube with a hollow lumen, and the outflow conduit can have a second flexible tube with a hollow lumen. The inflow conduit can be a first lumen of a flexible tube, and the outflow conduit can be a second hollow lumen of the flexible tube.

The methods can further include: (d) detecting the temperature of the fluid in the inflow conduit, and detecting the temperature of the fluid in the ouflow conduit; (e) calculating the amount of calories lost using the formula:

$$\text{Kcal lost/minute} = (T_o - T_i) \times \text{flow (L/min)} \times \text{specific heat capacity of the fluid,}$$

where To is the temperature of the fluid in the ouflow conduit and Ti is the temperature of the fluid in the inflow conduit; and (f) based on the calculated calorie loss, adjusting the pump to infuse the fluid more rapidly or more slowly into the inflatable member, to reach a target rate of calorie loss. The target rate of calorie loss can be four to ten Kcal/minute.

The methods can further include monitoring the patient's core temperature, and if the patient's core temperature drops by 1° C. or more, adjusting the pump to infuse the fluid more slowly into the inflatable member, or turning the pump off.

The device can have one or more sensors to detect temperature and/or pressure at one or more of the inflow conduit, the outflow conduit, and the inflatable member, and the device can be operably connected to a pump adapted to infuse the fluid into the inflatable member and remove the fluid from the inflatable member, and to a controller adapted to control the rate at which the fluid is pumped into and out of the inflatable member. For example, the device can have an inflow conduit sensor to detect a temperature of the fluid at the inflow conduit and to send a signal regarding temperature at the inflow conduit to the controller, and an outflow conduit sensor to detect a temperature of the fluid at the outflow conduit and to send a signal regarding temperature at the outflow conduit to the controller, where the inflow conduit sensor detects the temperature of the fluid in the inflow conduit and sends a signal regarding the inflow conduit temperature to the controller, the outflow conduit sensor detects the temperature of the fluid in the ouflow conduit and sends a signal regarding the outflow conduit temperature to the controller, the controller calculates the amount of calories lost using the formula:

Kcal lost/minute=($T_o$-$T_i$)×flow (L/min)×specific heat capacity of the fluid, where To is the temperature of the fluid in the ouflow conduit and Ti is the temperature of the fluid in the inflow conduit, and based on the calculated calorie loss, the controller can cause the pump to infuse the fluid more rapidly or more slowly into the inflatable member, to reach a target rate of calorie loss. The target rate of calorie loss can be four to ten Kcal/minute.

The method can further include using a sensor adapted to detect a core body temperature of the patient and to send a signal regarding the core body temperature to the controller, and if the patient's core temperature drops by 1° C. or more, the controller can cause the pump to infuse the fluid more slowly into the inflatable member, or turns the pump off.

The inflatable member can be inserted into the stomach or the duodenum of the patient. The inflatable member can have an inner layer and an outer layer. The device can be inserted into the patient via the mouth or nose of the patient, or can be inserted into the patient percutaneously.

The device can have a retention means adapted for retaining the inflatable member at a desired location. The retention means can be a balloon, and the method can further include filling the retention means with a fluid.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 4 is a side view of another implementation of an exemplary apparatus placed in the stomach of a subject.

FIG. 5 is a block diagram of another design of the apparatus of FIG. 1 and its associated control system.

FIG. 6 is a side view of at least a portion of the apparatus of FIG. 5, contained within an outer sheath.

DESCRIPTION

Figure 1:
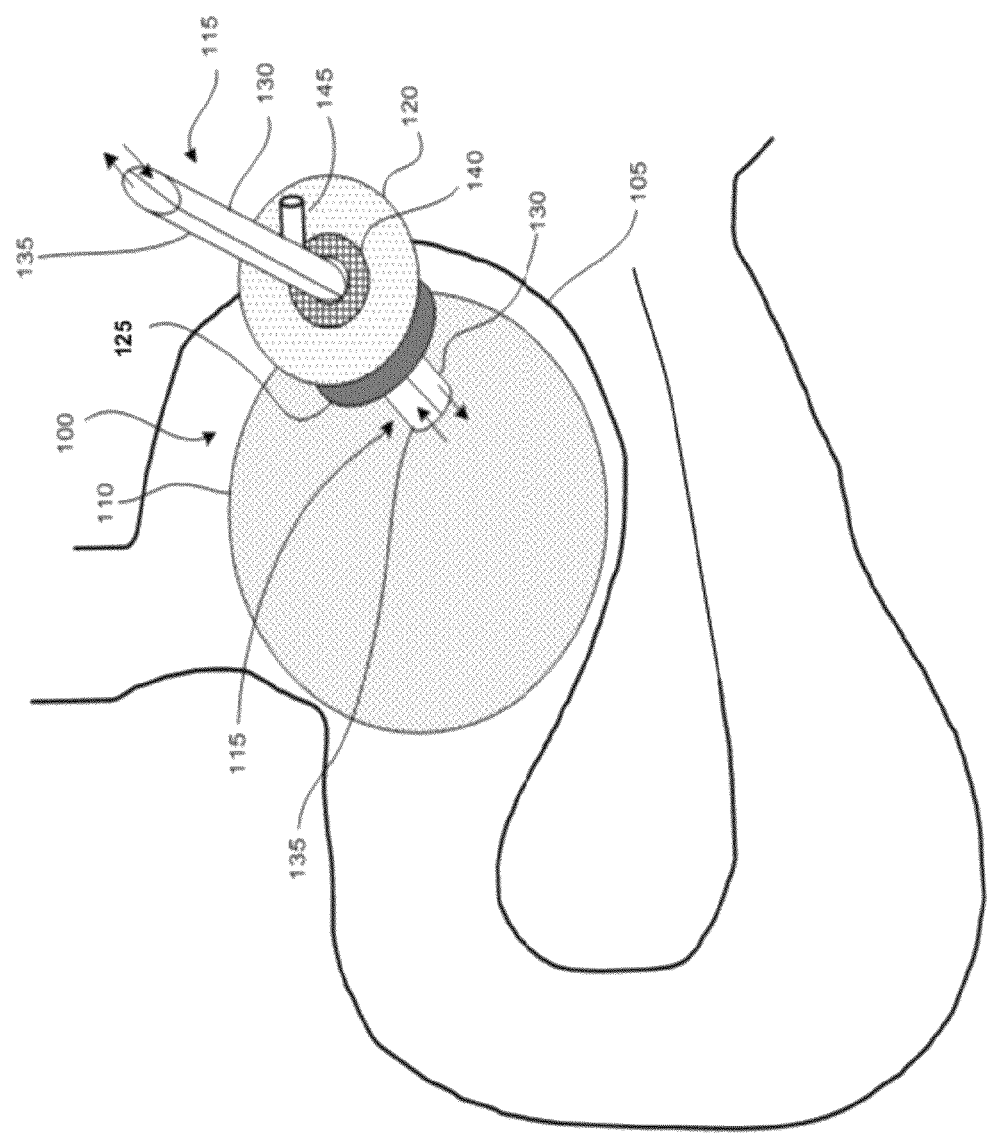
FIG. 1 is a side view of an exemplary apparatus placed in the stomach of a subject.

As described herein, weight related disorders such as obesity can be treated using localized hypothermia, while avoiding generalized hypothermia. The localized hypothermia can be, in some examples, gastric hypothermia, duodenal hypothermia, or gastroduodenal hypothermia. Generally, the localized hypothermia can be applied to a part of the body, to an organ such as the stomach or small intestine, or to a limb or to the trunk, either alternating, alone, or in combination. For example, obesity can be treated using one or more balloons placed in the stomach, in the duodenum adjacent to the stomach, or in both the stomach and the duodenum. In this treatment, a balloon can be perfused with a relatively cold fluid (i.e., a fluid that is at a lower temperature than the body temperature) to cause hypothermia localized to the region of the body in which the balloon is placed, resulting in a thermal gradient between the local cold region and the rest of the person's body. Because of this thermal gradient, heat is transferred from the person's body toward the local cold region, and that heat can be evacuated from the region through the fluid path out of the balloon and out of the patient.

A body part also can be subjected to localized hypothermia by applying an apparatus having a heat conductive material to the body part of the patient, to enable a heat exchange between the body part and the heat conductive material. The body part can be subjected to localized hypothermia by inserting the apparatus into the patient or by applying the apparatus to an external body part of the patient. The apparatus also may be simultaneously applied to another body part of the patient.

In some implementations, for example, a body part can be subjected to localized hypothermia by applying to the body part an apparatus comprising one or more cooling balloons, and filling all or a portion of at least one of the one or more cooling balloons with a fluid having a temperature from about 2° C. to about 35° C. (e.g., about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35° C.). For example, a fluid in the one or more cooling balloons can have a temperature of about 25° C., about 30° C., or about 35° C.

Localized hypothermia can be achieved using, for example, cold (e.g., 4° C.) water as a cooling liquid that flows through a balloon. Water cools more efficiently than ethanol at the same temperature, as water has a specific heat capacity that is 2.2 times higher than that of ethanol (4.2 J cm$^{-3}$ K$^{-1}$ for water vs. 1.9 J cm$^{-3}$ K$^{-1}$ for ethanol). In a person having a body temperature of 37° C., an approximate infusion rate of 1.0 liters of water per minute at 4° C. should result in an outflow temperature that is 4 to 9° C. warmer that the infused water (that is, 8-13° C.). Thus, gastric freezing can be prevented. Such an infusion or fluid flow rate and fluid temperature can result in a 4-9 Kcal/minute loss, which is similar to the loss achieved with moderate to strenuous exercise. By adjusting the flow rate and/or the fluid temperature, the amount of calories lost also can be adjusted. In some implementation, the flow rate and temperature can be adjusted to allow for loss of about three to 50 Kcal/hour (e.g., three, four, five, six, seven, eight, nine, ten, 15, 20, 25, 30, 35, 40, 45, or 50 Kcal/hour.

A gradual loss of a few calories to several hundred calories per hour can be comfortably achieved in humans in a safe manner, using a localized hypothermia apparatus with proper standardization of the equipment and methods, and building in safety features for the apparatus, in addition to choosing the appropriate patient and ruling out contraindications that might make the risks of using the apparatus outweigh the benefits. General contraindications may include any of the following: ongoing coronary ischemia, stroke, aspiration, pneumonia, liver, kidney or heart failure, moderate to severe lung disease (e.g., hypoxia, COPD, pulmonary hypertension, ARDS, pulmonary edema or hemorrhage, interstitial lung disease, pneumothorax, or pleural effusions), hypotension, hypothermia, malignancy, and local or systemic infections. Contraindications specific to a gastric and/or duodenal balloon device can include, for example, gastric or intestinal vascular malformations, varices (gastric or esophageal), ulcers, large esophageal hernia, previous gastric surgery or malformations, perforation, bleeding disorders, gastrointestinal bleeding, persistent retching, dry heaves, nausea or vomiting, and gastric outlet or intestinal obstruction. Contraindications to cooling the limbs and the trunk include, but are not limited to: trauma, burns, ulcers, skin breakdown, fractures, dislocation, infections such as abscesses, pyoderma, cellulitis, facitis, osteomylitis, septic arthritis, rhabdomyolysis, myositis, ischemia, arterial or venous thrombosis, a hypercoagulable state, and neuropathy. Other contraindications can include significant pathology that may be masked, worsen, or progress during the course of therapy, as well as impaired decision making or inability to activate an emergency medical response.

Referring to FIG. 1, an exemplary apparatus 100 is designed to provide localized hypothermia in a stomach 105 of a patient to cause a loss of calories and thereby facilitate weight loss in the patient. The principle and functioning of the treatment described for the stomach 105 can be adapted for the duodenum or other parts of the body, such as the limbs or the trunk, either alone, alternating, or in combination. The apparatus 100 includes an inflatable member (e.g., balloon 110) that is placed in the patient's stomach 105. Balloon 110 may be referred to as a "gastric balloon." It is to be noted that in some implementations, an apparatus can include a duodenal balloon in addition to or instead of a gastric balloon, where the duodenal balloon is configured for placement in the duodenum. In some implementations, a device can include more than one duodenal balloon and/or more than one gastric balloon.

The balloon 110 is attached to a hollow tube 115 that extends from the balloon 110 through the patient's body surface 120 to an area external to the patient, to allow for connection to an external control system, for example. In some implementations, including that depicted in FIG. 1, the hollow tube 115 and the balloon 110 can be placed percutaneously, such that tube 115 passes through the abdominal wall. In other implementations, the apparatus 100 can be placed through the nose or mouth, for example, endoscopically. Percutaneous placement of the apparatus 100 can provide patients with greater comfort and mobility than placement through the nose or mouth, however. In addition, patients with a percutaneously-placed apparatus may be treated on an outpatient basis.

As shown in FIG. 1, the tube 115 includes two passageways (or lumens). An inflow passageway 130 allows the flow of a fluid into the balloon 110, and an outflow passageway 135 allows flow of the fluid out of the balloon 110. Fluid flowing into the balloon 110 through the inflow passageway 130 is at a temperature below the body temperature of the patient, and fluid flowing out of the balloon 110 through the outflow passageway 135 has warmed up relative to its temperature upon entry into the balloon 110, due to heat transfer between the patient's stomach and the fluid in the balloon 110. It is to be noted that in some implementations, an apparatus can have separate tubes providing inflow and outflow channels to and from the balloon.

The interior of the balloon 110 is in fluid communication with the inflow passageway 130, through which fluid can be passed into the balloon 110, and the outflow passageway 135, through which fluid can be removed from the balloon 110. The tube 115 can be made of a flexible material including, without limitation, plastic, silicone, rubber, polyurethane, or nitrile, and can be calibrated along its length. The balloon 110 can be made of an elastic or non-elastic material, including, without limitation, latex, plastic, polyethylene, nitrile, cellophane, rubber, silicone, polyurethane, or other materials that can conform to the contours of the surrounding structures. In some implementations, the balloon 110 has two layers—an inner layer and an outer later. Such inner and outer layers can be made from the same material, or from different materials.

In some implementations, the apparatus 100 includes a means for retaining the balloon 110 in the proper position within a patient. For example, the apparatus 100 can have a bumper 125 positioned next to a wall of the stomach 105 at the opening through which the tube 115 exits the stomach 105. The bumper 125 can be about 10-30 mm (e.g., about 10, 12, 15, 17, 20, 22, 25, 27, or 30 mm) in diameter, and can be made of a flexible material such as, for example, rubber, silicone, or polyurethane. The bumper 125 can prevent the gastric balloon 110 from being pulled out of the stomach 105 via the opening through which the tube 115 exits the stomach 105.

The apparatus 100 also can include a guard 140 that can protect the patient's skin at the opening through which the tube 115 passes through the patient's body surface 120. The guard 140 can provide a mechanical reinforcement much like a grommet, and therefore can help to keep the tube 115 from moving relative to the patient's body, thus reducing the possibility of the apparatus 100 migrating into the stomach 105 or beyond, and reducing the possibility of irritation, chafing, or damage to the skin.

Fluid inflow and outflow can occur simultaneously or on an alternating basis, and can provide continuous perfusion to maintain a generally constant temperature of the fluid in the balloon 110. Continuous perfusion can be conducted at a constant pressure or by actively perfusing and suctioning out a constant volume at the same time. In some implementations, the apparatus 100 can include a port through which the pressure within the balloon 110 can be monitored. As depicted in FIG. 1, for example, a pressure monitoring port 145 can be part of the tube 115. The port 145 can provide an access point for a pressure sensing device, which can extend through the port 145 and into the tube 115 or, in some implementations, into the balloon 120.

The apparatus 100 can have any suitable dimensions. In some implementations, the tube 115 can have a length from about six inches to about ten feet (e.g., about six or nine inches, or about one, two, three, four, five, six, seven, eight, nine, or ten feet). When the tube 115 is placed through the nose or mouth, for example, the tube 115 can have a length sufficient to extend from the nose or mouth to the stomach, plus enough length at the distal end (away from the patient) for connection with one or more control apparatuses (e.g., pumps or sensors for monitoring temperature and/or pressure). Further, the balloon 110 can have an uninflated diameter suitable for passage through the mouth, the nose, the esophagus, or an endoscope. For example, the uninflated diameter of the balloon 110 can range from about one mm to about 20 mm (e.g., about one, two, three, four, five, six, seven, eight, nine, ten, 11, 12, 13, 14, 15, 16, 17, 18, 19, or 20 mm). In addition, the balloon 110 can have a fluid capacity from about 0.5 to about 4 liters (e.g., about 0.5, 0.75, 1, 1.5, 2, 2.5, 3, 3.5, or 4 liters).

Figure 2:
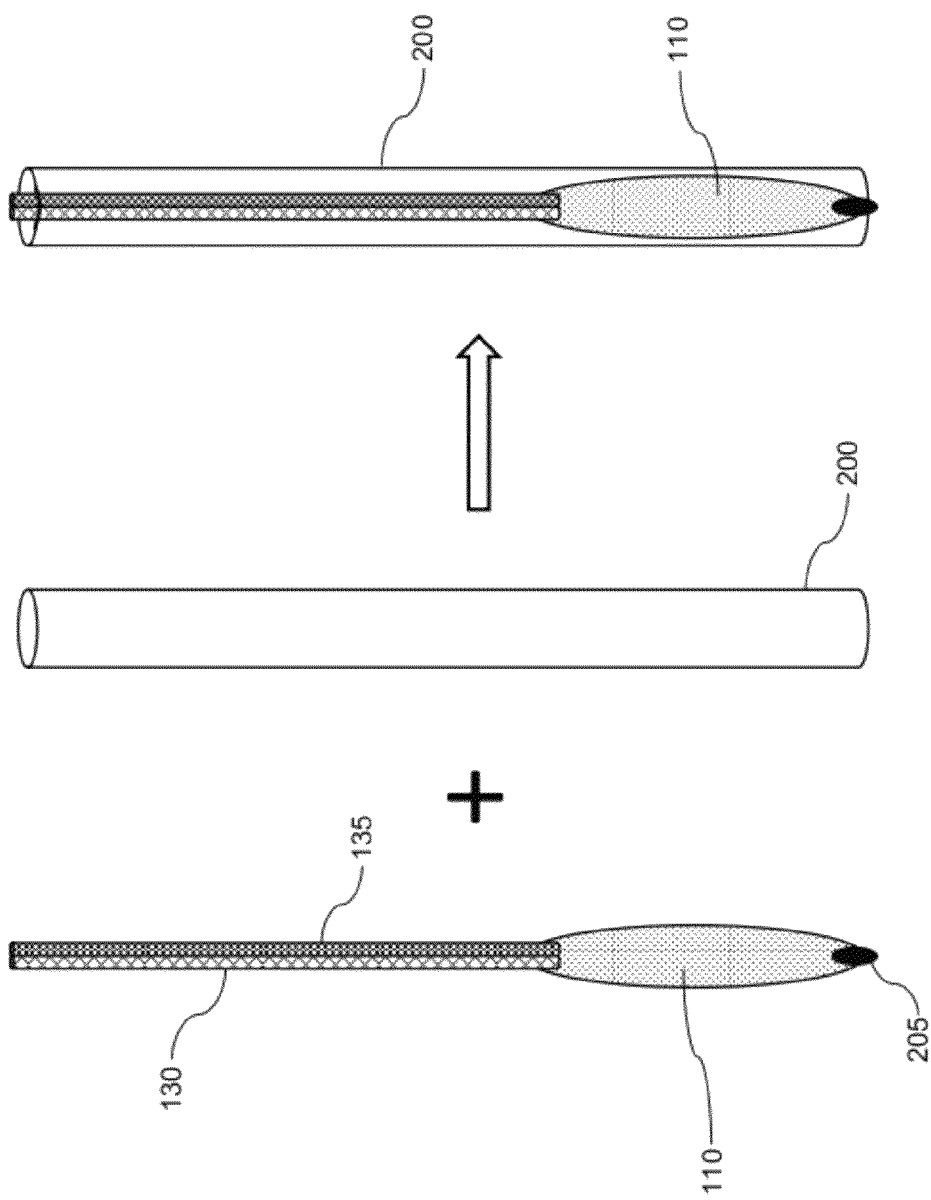
FIG. 2 is a side view of at least a portion of the apparatus of FIG. 1, contained within an outer sheath.

Referring also to FIG. 2, in some implementations, all or a portion of the apparatus 100 can be contained within an elongate, flexible outer sheath 200 prior to placement in a patient. In use, the outer sheath 200 containing all or a portion of the apparatus 100 can be inserted into the patient. The outer sheath 200 then can be removed, and the balloon 110 can be inflated through the tube 115. In some cases, the balloon 110 can have a weighted distal tip 205, which can facilitate nasogastric, orogastric, or percutaneous placement of the balloon 110 within the patient.

Figure 3:
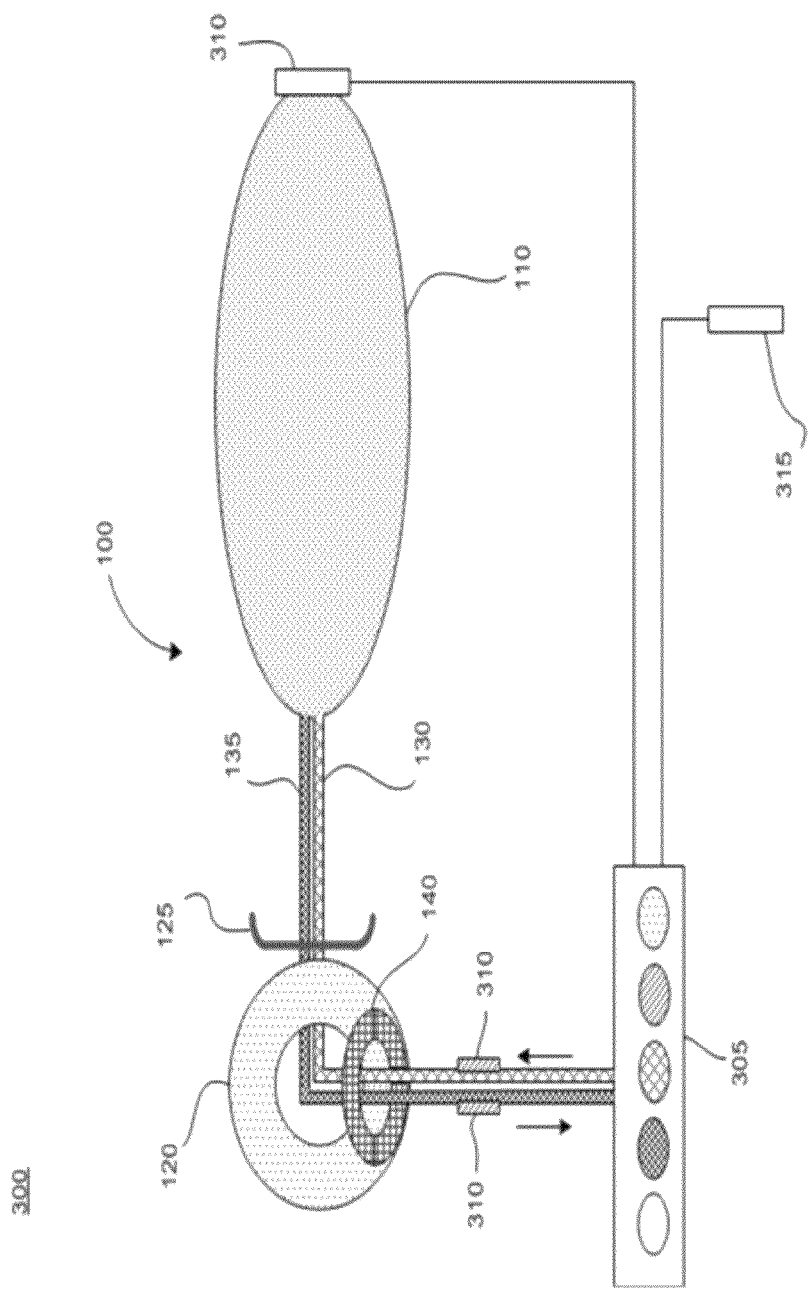
FIG. 3 is a block diagram of the apparatus of FIG. 1 and its associated control system.

Referring also to FIG. 3, the apparatus 100 can be part of a system 300 that also includes a controller 305 and one or more sensors 310. The controller 305 can include a fluid flow pump for pumping fluid into the inflow passageway 130 and for pumping fluid out of the outflow passageway 135. The controller 305 also can include a refrigeration system for cooling fluid from the outflow passageway 135 before the fluid is redirected into the inflow passageway 130. The one or more sensors 310 can sense one or more of temperature, pressure, and volume of the fluid in the balloon 110 and/or in passageways 130 and 135; pressure and temperature of the balloon 110, and volume and placement of the apparatus 100 typically are closely monitored during use. In some implementations, the sensors 310 are temperature sensors located at the inflow passageway 130 and at the outflow passageway 135. In such implementations, the sensors 310 can measure the temperature of the fluid flowing into and out of the balloon 110 through the inflow and outflow passageways 130 and 135, respectively. In some implementations, a sensor 310 can be a thermocouple placed in the wall of the outflow passageway 135, the wall of the inflow passageway 130, or the wall of the balloon 110.

In some implementations for operation of the system 300, the sheath 200 containing the apparatus 100 (with the balloon 110 in a deflated configuration) can be inserted percutaneously into a patient, such that the balloon 110 is placed within the stomach. The sheath 200 can be removed from the patient's body, and the bumper 125 can be permitted to adjust either by virtue of flexibility of the material from which it is made (e.g., polyurethane), through an active adjustment mechanism, or through a spring mechanism, such that it is positioned adjacent to a wall of the stomach 105. The skin guard 140 can be passed over the tube 115, and the tube 115 can be connected to the refrigeration system and the pump of the controller 305. The balloon 110 can be inflated (for example, to a pressure that is less than or equal to normal gastric pressure after a meal) with a cold fluid (e.g., water, saline, or a gas). The fluid can have an inflow temperature between about 2 and about 35° C. (e.g., about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35° C.), and can be passed into the balloon 110 at a flow rate of about 0.1 to 4 liters/minute (e.g., about 0.1, 0.2, 0.3, 0.5, 0.7, 0.8, 1, 1.2, 1.3, 1.5, 1.7, 1.8, 2, 2.2, 2.4, 2.6, 2.8, 3, 3.2, 3.4, 3.6, 3.8, or 4 liters/minute). In some implementations, the balloon 110 can be irrigated with fluid at a particular pressure, for example, between about 1 and about 25 mm Hg (e.g., about 1, 2, 3, 4, 5, 6, 7, 8, 9, 10, 11, 12, 13, 14, 15, 16, 17, 18, 19, 20, 21, 22, 23, 24 or 25 mm Hg).

The flow rate and the temperature of the fluid that flows into the inflow passageway 130 can be adjusted by the controller 305, based on a calculation that determines the Kcal lost/minute. The control system 300 can calculate an amount of calories being lost while using the apparatus 100, using the following formula:

$$\text{Kcal lost/minute} = (T_o - T_i) \times \text{Flow (L/min)} \times \text{specific heat capacity of the fluid.}$$

That is, the rate of flow is multiplied by the difference between inflow temperature ($T_i$) and outflow temperature ($T_o$) (in ° C. or K), and the resulting product is multiplied the product by the specific heat capacity of the fluid used for irrigation (for example, the specific heat capacity of water is 1 and of ethanol is 0.46). The resulting number provides a measure of calories lost in Kcal/minute.

By adjusting the flow rate and/or the temperature of the infused fluid, the rate of cooling can be controlled. In some implementations, the rate of cooling can be gradually escalated over several hours or days (e.g., starting at losing about 0.5 Kcal/minute and gradually escalating this such that about 10 Kcal/minute are lost). Suitable rates of cooling can range from about 0.5 Kcal/minute to about 50 Kcal/minute or more (e.g., about 0.5, one, two, three, four, five, six, seven, eight, nine, ten, 15, 20, 25, 30, 35, 40, 45, 50, or more than 50 Kcal/minute).

The controller 305 also can receive information about other parameters (e.g., temperature) that are measured at one or more sensors 315 placed at other locations within or on a patient's body. In this way, the controller 305 can determine whether there is an unacceptable drop in body temperature (e.g., greater than 1 or 2° C.), and can provide an automatic shut off of the apparatus 100 if an unacceptable drop in body temperature occurs. The sensed temperature can be retrieved by the controller 305 remotely (e.g., by infrared signal) or by hard wiring. In some implementations, the controller 305 also can include a system to warm a fluid and pump it in place of the cooling fluid if, for example, the sensor 315 notes an unacceptable drop in body temperature.

In some implementations, the balloon 110 can be held in place with another balloon (e.g., a pre-pyloric balloon or an esophageal balloon, or both) that is maintained in a continuously inflated state with, for example, a radio-opaque fluid such as HYPAQUE™. Any of the balloons (e.g., balloon 110 or a pre-pyloric or esophageal balloon) can be designed to automatically deflate and activate an alarm if a sensed pressure in the apparatus 100 exceeds a certain level (e.g., 50 mm Hg for three minutes or more). Such a mechanism can prevent distal migration of the tube 115 and/or the apparatus 100.

In some implementations, the apparatus 100 can be percutaneously inserted into a patient. Methods for percutaneous placement include, without limitation, percutaneous endoscopic gastroscopy (PEG), which is an endoscopic procedure for placing a tube into the stomach through the abdominal wall. Techniques for placing PEG tubes are known in the art, and can include performing a gastroscopy to evaluate the anatomy of the stomach, identifying the anterior stomach wall, ensuring that no organs are present between the wall and the skin, and puncturing the abdominal wall through a small incision using an angiocath. In some cases, a wire can be placed into the stomach, and a series of dilators can be used to increase the size of the passage through the skin and abdominal wall. An endoscope can be passed through the channel into the stomach after the channel has matured (over the course of several weeks, for example), and the apparatus 100 can be placed in the patient using the endoscope with or without a guide wire or fluoroscopic guidance. In some implementations, the apparatus 100 can initially be placed in a patient through the mouth or nose, and then can be replaced by another apparatus that is placed percutaneously (e.g., for long-term treatment). This can be useful, for example, to begin hypothermia treatment quickly, while allowing for eventual treatment that gives the patient relatively more comfort and freedom of mobility.

In other implementations, the tube 115 can be placed using a preexisting PEG site. In such cases, the tube 115 may lack attachments that could otherwise be used for engaging a guide wire to pull the tube through the incision of a new PEG site. Instead, the tube 115 can be gently pushed through a preexisting PEG tube of appropriate size. Location of the tube 115 can be verified endoscopically, for example.

In some implementations, the apparatus 100 can include one or more radio-opaque markers (e.g., on the balloon 110), and the location of the apparatus 100 and/or the balloon 110 can be monitored using x-ray.

Turning now to FIG. 4, in some implementations, a device other than a cooled balloon is used to provide localized hypothermia to the stomach or another organ. For example, a cooling device 410 can be placed in contact with the wall of an internal organ (e.g., the stomach), and can cool the organ with a conductive material such as cool conductive metal wires, plates, spheres, ovals, ellipsoids, or conoids. The device 410 can be configured and placed to provide for sufficient heat exchange between the organ wall and the device 410, permitting heat transfer away from the organ. To prevent erosion and pressure necrosis, and to conform the device 410 to the shape of the organ (or part of the organ) that it will contact, the cooling device 410 can be covered with one or more synthetic and pliable, heat conductive materials such as, for example, Teflon, polyethylene, plastic, cellophane, rubber or other natural or synthetic polymeric soft conductive materials, or a combination thereof. The cooling device 410 can be controlled by one or more electrical wires 430 that extend to the controller (e.g., controller 305).

Referring also to FIGS. 5 and 6, the apparatus 100 can have a "bumper" balloon 525 adapted to be positioned next to the stomach wall at the opening through which the tube 115 was inserted. Typically, a bumper balloon 525 is used after the opening has matured, and is not used at the time the apparatus 100 is initially place. Inflation of the bumper balloon 525 can prevent the balloon 110 from being pulled out of the stomach 105 through the opening through which the tube 115 was inserted. If the bumper balloon 525 is included, the apparatus 100 also can include a tube 545 having a lumen that is in fluid communication with the interior of the bumper balloon 525, to permit inflation or deflation of the bumper balloon 525 with a fluid (e.g., a liquid or a gas).

In such implementations, both the balloon 110 and the bumper balloon 525 can be contained within the outer sheath 200. In use, the apparatus 100 (or a portion thereof) and the outer sheath 200 can be positioned in the patient, the outer sheath 200 can be removed, the balloon 110 can be inflated with a fluid via the tube 115, and the bumper balloon 525 can be inflated with a fluid via the tube 545.

For localized hypothermia at other parts of the body (e.g., limbs or trunk), the apparatus 100 can be used with the following exemplary modifications. The balloon 110 or other conductive materials mentioned herein can be configured to cover all or a part of the limb or trunk. In such cases, any of the bumper 125 or bumper balloon 525, the skin guard 140, the sheath 200, the port 145, any retention balloons, and the weighted tip 205 may be omitted. In some embodiments, the cooling device 410 can be used, and can have an additional temperature sensor 310 on its surface to monitor the surface temperature of the limb or the trunk. The limb or trunk cooling can be done for a period of, for example, 1 to 60 minutes (e.g., 1, 2, 5, 10, 15, 20, 25, 30, 35, 40, 45, 50, 55, or 60 minutes), and then stopped. Another part of the body then can be cooled, while the initial area is allowed to warm on its own. Further cooling of a previously cooled body part can be delayed until that part regains a temperature higher than 0.5° C. below its initial baseline temperature.

The apparatus 100 can provide for rapid calorie and weight loss without major life style changes. In appropriate patients, for example, the apparatus 100 or 400 can be used in an ambulatory setting with little or no supervision, and patients can continue with their regular daily activities. The apparatus 100 or 400 requires no complicated surgery (e.g., bariatric surgery) or associated long term complications. Moreover, no long term drugs are required. The apparatus 100 or 400 also can be removed when appropriate, with prompt reversal of the PEG site (in the case of apparatus 100) and restoration of previous anatomy. The apparatus 100 or 400 can be left in place in or on a patient for any suitable length of time. A cooled gastric balloon, for example, when placed within a patient's stomach via PEG, can remain in the patient for up to six months or more (e.g., several days, one, two, three, or four weeks, or one, two, three, four, five, or six months, or even longer).

In a general aspect, a method for treating obesity in a patient includes subjecting a part of the body of the patient to localized hypothermia, thereby causing a caloric loss in the patient and offsetting caloric intake in the patient. Body parts that can be subjected to localized hypothermia include, for example, organs (e.g., the stomach, the esophagus, or the small intestine), limbs, the trunk, and the tissue. In some implementations, for example, the stomach can be subjected to localized hypothermia.

In practice, a patient can be educated about the rationale and use of the apparatus 100. The patient should understand the procedures for placement and use of the apparatus, the risks and benefits of using the apparatus, and alternative treatments. The patient also should understand the safety mechanisms for the apparatus. After the patient masters the use of the apparatus and shows reliability and competence in its use, the patient can operate the apparatus with minimal supervision, possibly in an ambulatory setting.

The apparatus 100 also can be made to reduce the rate of calorie loss, to shut off, and/or to be more efficient for losing calories in an auto-regulatory manner by changing the temperature of the fluid and/or the flow rate of the fluid being used for irrigation. For example, the apparatus 100 can have an inbuilt safety mechanism to prevent systemic or generalized hypothermia, or an unacceptable drop in body temperature, by monitoring the temperature at another site (e.g., one or more of a tympanic, oral, axillary, rectal, or forehead site) using the one or more sensors 315. The controller 305 then can compare the monitored temperature to the basal temperature. If there is an unacceptable drop in temperature, the apparatus 100 can have mechanisms to shut off on its own, suck out the cold fluid, and/or perfuse the balloon 110 with warmer fluid.

Other safety mechanisms also can be built into or used with the apparatus 100 and the system 300, and can be verified before the apparatus is used. Such safety mechanisms include, for example, any one or more of the following:

having a medical professional who is competent in placing PEG tubes and endoscopy put the apparatus into place.

using the apparatus only when the patient is awake and alert;

ensuring that the patient has access to blankets and/or an emergency alert system (e.g., a telephone to alert emergency medical personnel);

using the apparatus only in patients who are competent to operate it, and who can promptly ask for help if they sense there is a problem with the device (e.g., skin breakdown, bleeding, pain, or pus drainage);

using a balloon that is double layered, such that it has an inner layer and an outer layer, where if the inner layer tears or bursts, fluid coming into contact with the inner surface of the outer balloon triggers the infusion pump to immediately stop, and activates a suction device to empty the balloon;

positioning a bumper on the tube next to the inner surface of the stomach at the opening through which the tube passes into the stomach, and/or positioning a protective device around the tube and against the skin at the opening, to prevent the apparatus from slipping;

including a sensor such that excess traction of the tubing or excess fluid pressure (e.g., pressure above 10 mm Hg) activates a suction device to empty the balloon and trigger an alarm; and using an apparatus that does not include any corrosive, dangerous, explosive, carcinogenic, or teratogenic fluids or materials.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a weight disorder in a patient in need thereof, comprising subjecting an organ or tissue of the patient to localized hypothermia by:
   (a) inserting into the patient a device comprising an inflatable member having an interior and an exterior, and an inflow conduit and an outflow conduit in fluid communication with the interior of the inflatable member;
   (b) infusing the inflatable member with a fluid passed through the inflow conduit, wherein the fluid is at a temperature from about 4° C. to about 35° C.; and
   (c) removing fluid from the inflatable member through the outflow conduit.

2. The method of claim 1, wherein the weight disorder is obesity, and wherein the patient has a body mass index of at least 30 kg/m².

3. The method of claim 1, wherein the fluid has a temperature of about 30-35° C. when it is infused into the inflatable member.

4. The method of claim 1, wherein the fluid is water.

5. The method of claim 1, wherein the inflow conduit comprises a first flexible tube having a hollow lumen, and the outflow conduit comprises a second flexible tube having a hollow lumen.

6. The method of claim 1, wherein the inflow conduit comprises a first lumen of a flexible tube, and wherein the outflow conduit comprises a second hollow lumen of the flexible tube.

7. The method of claim 1, further comprising:
   (d) detecting the temperature of the fluid in the inflow conduit, and detecting the temperature of the fluid in the outflow conduit;
   (e) calculating the amount of calories lost using the formula:

$$\text{Kcal lost/minute} = (T_o - T_i) \times \text{flow (L/min)} \times \text{specific heat capacity of the fluid,}$$

where $T_o$ is the temperature of the fluid in the ouflow conduit and $T_i$ is the temperature of the fluid in the inflow conduit; and
   (f) based on the calculated calorie loss, adjusting the pump to infuse the fluid more rapidly or more slowly into the inflatable member, to reach a target rate of calorie loss.

8. The method of claim 7, wherein the target rate of calorie loss is four to ten Kcal/minute.

9. The method of claim 7, further comprising monitoring the patient's core temperature, and if the patient's core temperature drops by 1° C. or more, adjusting the pump to infuse the fluid more slowly into the inflatable member, or turning the pump off.

10. The method of claim 1, wherein the device comprises one or more sensors to detect temperature and/or pressure at one or more of the inflow conduit, the outflow conduit, and the inflatable member, and wherein the device is operably connected to a pump adapted to infuse the fluid into the inflatable member and remove the fluid from the inflatable member, and to a controller adapted to control the rate at which the fluid is pumped into and out of the inflatable member.

11. The method of claim 10, wherein the device comprises an inflow conduit sensor to detect a temperature of the fluid at the inflow conduit and to send a signal regarding temperature at the inflow conduit to the controller, and an outflow conduit sensor to detect a temperature of the fluid at the outflow conduit and to send a signal regarding temperature at the outflow conduit to the controller, wherein:
   the inflow conduit sensor detects the temperature of the fluid in the inflow conduit and sends a signal regarding the inflow conduit temperature to the controller;
   the outflow conduit sensor detects the temperature of the fluid in the outflow conduit and sends a signal regarding the outflow conduit temperature to the controller;
   the controller calculates the amount of calories lost using the formula:

$$\text{Kcal lost/minute} = (T_o - T_i) \times \text{flow (L/min)} \times \text{specific heat capacity of the fluid,}$$

where $T_o$ is the temperature of the fluid in the outflow conduit and $T_i$ is the temperature of the fluid in the inflow conduit; and
   based on the calculated calorie loss, the controller causes the pump to infuse the fluid more rapidly or more slowly into the inflatable member, to reach a target rate of calorie loss.

12. The method of claim 11, wherein the target rate of calorie loss is four to ten Kcal/minute.

13. The method of claim 10, further comprising using a sensor adapted to detect a core body temperature of the patient and to send a signal regarding the core body temperature to the controller, wherein if the patient's core temperature drops by 1° C. or more, the controller causes the pump to infuse the fluid more slowly into the inflatable member, or turns the pump off.

14. The method of claim 1, wherein the inflatable member is inserted into the stomach or the duodenum of the patient.

15. The method of claim 1, wherein the inflatable member has an inner layer and an outer layer.

16. The method of claim 1, wherein the device is inserted into the patient via the mouth or nose of the patient.

17. The method of claim 1, wherein the device is inserted into the patient percutaneously.

18. The method of claim 1, wherein the device comprises a retention means adapted for retaining the inflatable member at a desired location.

19. The method of claim 18, wherein the retention means is a balloon, and wherein the method further comprises filling the retention means with a fluid.

* * * * *